(12) United States Patent
Viola et al.

(10) Patent No.: US 8,372,014 B2
(45) Date of Patent: Feb. 12, 2013

(54) POST-OPERATIVE BACTERIA TEST STRIP SPOOL AND METHOD

(75) Inventors: Frank J. Viola, Sandy Hook, CT (US); Michael A. Stolz, North Haven, CT (US); Robert J. Beetel, Hamden, CT (US); Katherine Jordan, Storrs, CT (US); Alicia Joy Farrell, Enfield, CT (US); Emily Grace-Anne Gumkowski, Redondo Beach, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/030,655

(22) Filed: Feb. 18, 2011

(65) Prior Publication Data

US 2011/0137139 A1    Jun. 9, 2011

Related U.S. Application Data

(62) Division of application No. 11/388,176, filed on Mar. 24, 2006, now Pat. No. 7,909,773.

(60) Provisional application No. 60/687,107, filed on Jun. 3, 2005.

(51) Int. Cl.
*A61B 5/00* (2006.01)
(52) U.S. Cl. .................................... 600/573
(58) Field of Classification Search .......... 600/574, 600/573, 347, 309, 345
See application file for complete search history.

(56) References Cited

U.S. PATENT DOCUMENTS

| 4,218,421 A | 8/1980 | Mack et al. |
|---|---|---|
| 5,035,704 A | 7/1991 | Lambert et al. |
| 5,181,905 A | 1/1993 | Flam |
| 5,314,804 A | 5/1994 | Boguslaski et al. |
| 5,341,803 A | 8/1994 | Goldberg et al. |
| 5,420,016 A | 5/1995 | Boguslaski et al. |
| 5,702,715 A | 12/1997 | Nikolaychik et al. |
| 5,744,150 A | 4/1998 | Cercone |
| 5,928,665 A | 7/1999 | Cercone |
| 6,197,325 B1 | 3/2001 | MacPhee et al. |
| 6,333,093 B1 | 12/2001 | Burrell et al. |
| 6,559,119 B1 | 5/2003 | Burgess et al. |
| 6,660,484 B2 | 12/2003 | Charych et al. |
| 7,276,027 B2 | 10/2007 | Haar et al. |
| 7,299,082 B2 * | 11/2007 | Feldman et al. .............. 600/347 |
| 7,455,451 B2 | 11/2008 | Pearl et al. |
| 7,465,286 B2 | 12/2008 | Patterson et al. |
| 2003/0040687 A1 | 2/2003 | Boynton et al. |
| 2003/0116598 A1 | 6/2003 | Huang |
| 2003/0143580 A1 | 7/2003 | Straus |
| 2004/0100376 A1 | 5/2004 | Lye et al. |
| 2004/0132217 A1 | 7/2004 | Prince et al. |
| 2006/0195128 A1 | 8/2006 | Alden et al. |

FOREIGN PATENT DOCUMENTS

| WO | WO 00/24438 A1 | 5/2000 |
|---|---|---|
| WO | WO 01/85637 A2 | 11/2001 |
| WO | WO 02/15955 A2 | 2/2002 |
| WO | WO 03/063693 A2 | 8/2003 |
| WO | WO 2004/056269 A1 | 7/2004 |
| WO | WO 2004/087942 A2 | 10/2004 |

\* cited by examiner

*Primary Examiner* — Jeffrey G Hoekstra
*Assistant Examiner* — Fangemonique Smith

(57) ABSTRACT

A method for testing body fluids is disclosed. The method includes providing a media-dispensing apparatus, placing at least the distal opening of the elongated tubular member adjacent body fluid (e.g., near a patient's abdomen) or adjacent a medical device such that a portion of the media strip contacts body fluid or the medical device, and advancing the media strip such that the portion of the media strip that contacted the body fluid or the medical device advances at least through the second lumen. Additionally, the step of cutting the media strip with a cutting instrument is also disclosed.

9 Claims, 3 Drawing Sheets

POST-OPERATIVE BACTERIA TEST STRIP SPOOL AND METHOD

CROSS-REFERENCE TO RELATED APPLICATIONS

The present application is a Divisional application of, claims the benefits of and priority to U.S. patent application Ser. No. 11/388,176 to Frank J. Viola, et al., filed on Mar. 24, 2006, which claims the benefits of and priority to U.S. Provisional Application No. 60/687,107, filed on Jun. 3, 2005, the entire contents of each of which are incorporated herein by reference.

BACKGROUND

1. Technical Field

The present disclosure relates generally to body fluid testing devices and methods, and more particularly, to a body fluid testing device and method that incorporates a post-operative test strip of material and a media-dispensing apparatus.

2. Background of the Art

Infection is a serious complication of implantable and insertable medical devices. The most common microorganisms causing these complications are *Staphylococcus epidermidis* and *Staphylococcus aureus*, which account for about two-thirds of cases of contamination or infection. Other gram-positive bacteria, gram-negative bacteria, viruses, and fungal microorganisms such as *Candida*, account for the remaining one-third of cases. Management of infected medical devices is very expensive and in most instances requires the removal of the infected device from the patient. Replacement medical devices must then be inserted or implanted in place of the contaminated medical device, which may require taking an X-ray to ensure proper insertion or implantation of the medical device. Accordingly, removal and replacement of medical devices is costly to hospitals and patients.

In patients with indwelling medical devices who develop fever, the possibility of device-related infection is considered. To accurately determine if the medical device is the source of infection, the medical device is typically removed and cultured to observe whether microbial activity is present on the medical device. Accordingly, even if the medical device turns out not to be the source of infection, it has already been removed, and a new medical device must be put in place of the suspect medical device. It has been reported that as much as 85% of indwelling central venous catheters that have been removed in suspicion of catheter-related infection yield sterile cultures. Thus, in as much as 85% of the time that medical devices are removed from patients, the medical devices themselves are not causing the fever, and the removal of them, in hindsight, was not necessary.

It has been observed that in the majority of cases where microbial contamination or infection of vascular catheters have been detected, the primary cause was dermal microbial colonization at the insertion or implantation site. The dermal microbial colonization migrated along the medical devices to colonize the medical devices at the interface between the medical device and the insertion or implantation site. This finding suggests that a prominent location to detect potentially pathogenic microbes would be at the medical device insertion or implantation site, and in some cases, on the external surface of the medical devices.

Infections are also attributed to leaks after suturing or stapling tissue, e.g., intestinal tissue. Intestinal contents have high concentrations of bacteria, which, if leaked into the abdomen, may lead to an inflammation or an infection. With current technology, it is difficult to detect the infection at an early stage when it is easiest to treat.

The acquisition and testing of body fluids is useful for many purposes and continues to grow in importance for use in medical diagnosis and treatment, and in other diverse applications. In the medical field, it is desirable for operators to be able to perform such tests routinely, quickly and reproducibly. Testing can be performed on various body fluids, and for certain applications is particularly related to the testing of blood and/or interstitial fluid. Such fluids can be tested for a variety of characteristics of the fluid, or analytes contained in the fluid, to identify a medical condition, determine therapeutic responses, assess the progress of treatment, and the like.

Various methods and apparatus for testing body fluids have been developed. These include inserting a syringe into a vein to withdraw a blood sample, making an incision in a patient's skin and collecting the blood in a container, and creating an incision and having patients urge fluid to the incision site by applying pressure to the area surrounding the incision. Sampling devices may be used to analyze the sample for a variety of properties or components. Such devices include, for example, systems in which a tube or test strip is either located adjacent the incision site prior to forming the incision, or is moved to the incision site shortly after the incision has been formed. The test strips in these systems include structure which react with the fluid to allow the sample to be analyzed. Such structure could allow for optical, electrochemical, and/or magnetic ways for analyzing the sampled fluid. One example of a testing device using a test media tape is disclosed in International Publication No. WO 2004/0005629 A1, the entire contents of which are incorporated by reference herein.

SUMMARY

The present disclosure is directed to a media-dispensing apparatus for testing body fluids. The apparatus includes a housing having a lower portion and an upper portion that are separated by a separator, and an elongated tubular member having a distal opening adjacent a distal end thereof. A first lumen is disposed within the elongated tubular member and extends from the lower portion of the housing to the distal opening. A second lumen is also disposed within the elongated tubular member and extends from the upper portion of the housing to the distal opening. A media strip (possibly a color changing medium which is able to detect or identify an abnormality or an infection) is dispensable from the lower portion of the housing (possibly around a central hub therein), through the first lumen, out of the distal opening of the elongated tubular member, through the second lumen and into the upper portion of the housing (and possibly through an aperture disposed through a portion of the upper portion).

In an embodiment of the present disclosure, a one-way passage valve is disposed within at least one of the housing, the elongated tubular member (e.g., the second lumen) and an interface therebetween. The one-way passage valve allows the media strip to travel in a single direction therethrough. In another disclosed embodiment, a seal is disposed within at least one of the first lumen (e.g., adjacent a distal end thereof) and the second lumen. The seal is configured to allow the media strip to pass therethrough and to limit the passage of body fluids.

In an embodiment of the present disclosure, at least a portion of a distal portion of the elongated tubular member is rounded or otherwise curved. Further, in a disclosed embodiment, one lumen (e.g., the first lumen) extends farther distally than the other lumen (e.g., the second lumen).

In a disclosed embodiment, a cover is hingedly coupled to the hosing. The cover is movable between a first position where the cover is in proximity with the upper portion of the housing and at least a second position where the cover is spaced apart from the upper portion of the housing. In an embodiment, a cutting instrument is disposed on a portion of at least one of the housing and the cover for cutting the media strip. In the embodiment where the cutting instrument is disposed on the cover, moving the cover from the second position to the first position cuts the media strip.

The present disclosure also relates to a method for testing body fluids. The method includes providing a media-dispensing apparatus, as described above, placing at least the distal opening of the elongated tubular member adjacent body fluid (e.g., near a patient's abdomen) or adjacent a medical device such that a portion of the media strip contacts body fluid or the medical device, and advancing the media strip such that the portion of the media strip that contacted the body fluid or the medical device advances at least through the second lumen. Additionally, the step of cutting the media strip with a cutting instrument is also disclosed.

In a disclosed method, a least a portion of the distal opening of the elongated tubular member remains adjacent body fluid or a medical device as the media strip is advanced.

BRIEF DESCRIPTION OF THE DRAWINGS

Embodiments of the present disclosure are described hereinbelow with reference to the drawings wherein.

DETAILED DESCRIPTION

Embodiments of the presently disclosed media-dispensing apparatus are described in detail with reference to the drawings wherein like numerals designate identical or corresponding elements in each of the several views. As is common in the art, the term 'proximal" refers to that part or component closer to the user or operator, e.g., surgeon, physician or nurse, while the term "distal" refers to that part or component farther away from the user.

Figure 1:
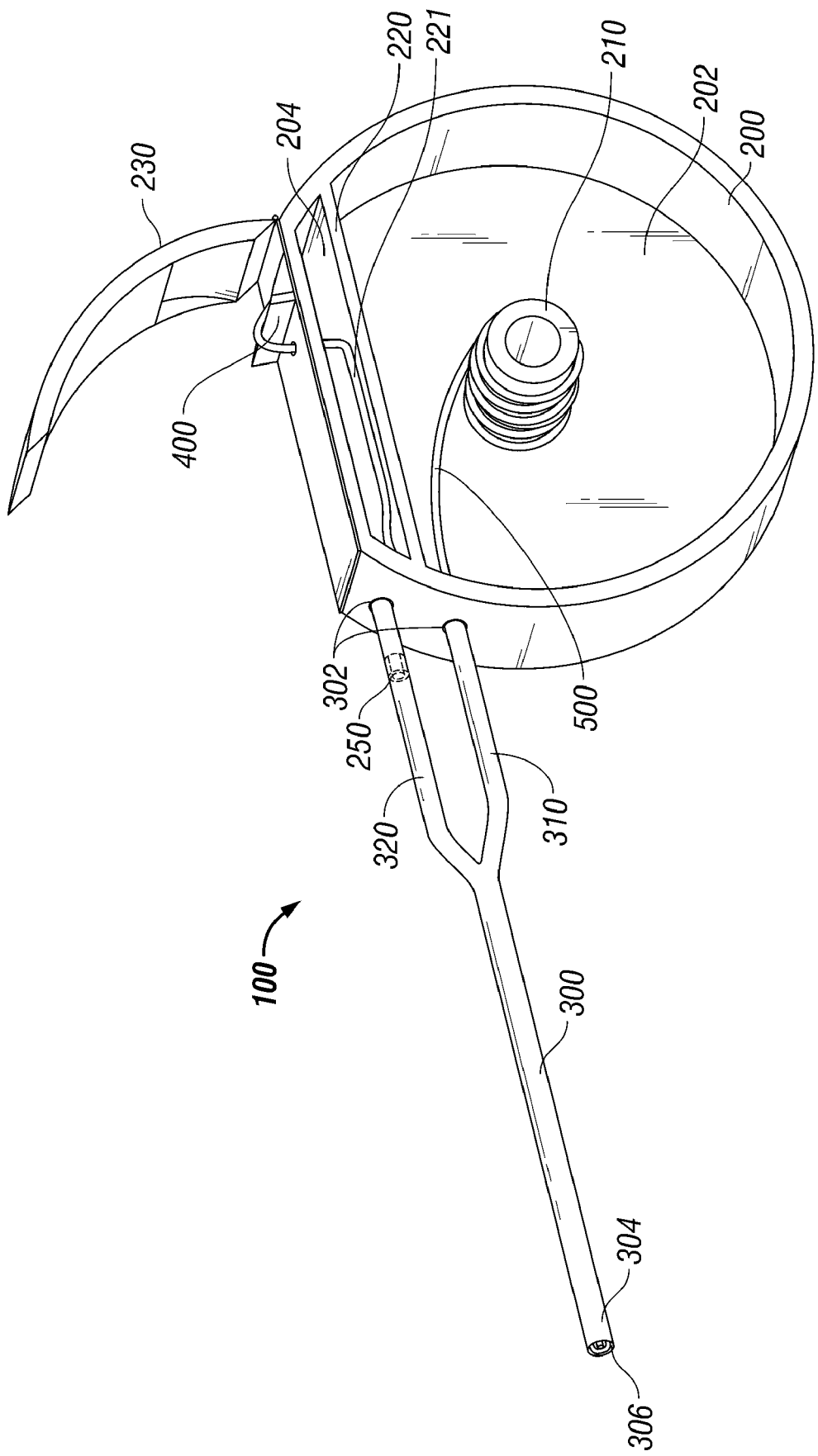
FIG. 1 is a perspective view of a media-dispensing apparatus according to an embodiment of the present disclosure.
Figure 2:
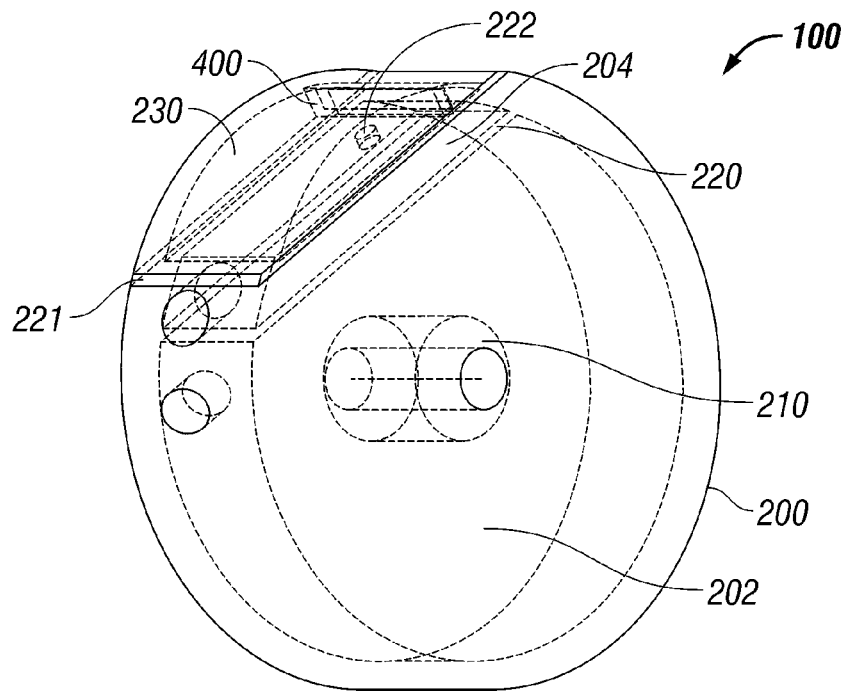
FIG. 2 is a perspective view of a housing and a cover of the media-dispensing apparatus of FIG. 1.
Figure 3:
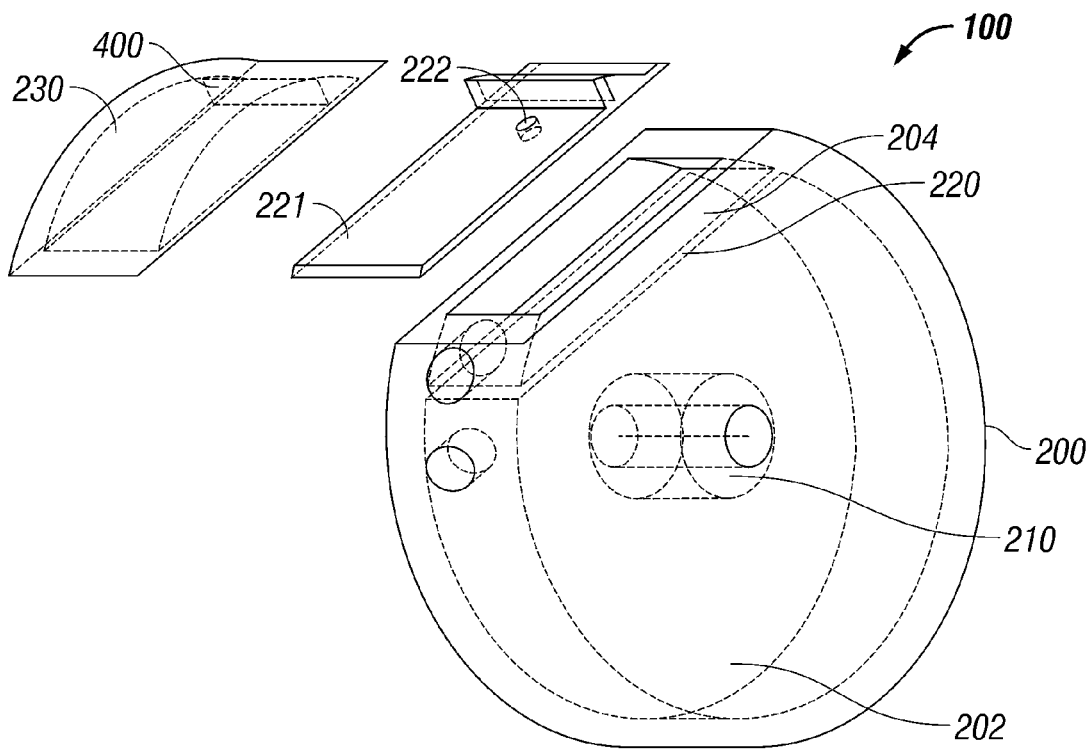
FIG. 3 is a perspective assembly drawing of the housing and cover of the media-dispensing apparatus of FIGS. 1 and 2, illustrated with a separator, a knife and the cover separated from the housing.

FIGS. 1-3 illustrate a media-dispensing apparatus of the present disclosure which is generally indicated by reference numeral 100. Media-dispensing apparatus 100 is configured to dispense a media strip 500 and includes a housing 200 and an elongated tubular member 300. In the embodiment illustrated in FIGS. 1-3, housing 200 includes a central hub 210, a separator 220 and a cover 230. Elongated tubular member 300 includes a proximal portion 302, a distal portion 304 and a distal opening 306. Elongated tubular member 300 also includes a first lumen 310 and a second lumen 320 extending therethrough. Proximal portion 302 of elongated tubular member 300 is operatively connected to housing 200.

More specifically, housing 200 includes a lower portion 202 where media strip 500 is initially placed and an upper portion 204 where media strip 500 is directed to after media strip 500 is pulled through second lumen 320 of elongated tubular member 300. Housing 200 may have a general shape of a short cylinder, as shown in FIGS. 1-3 and may be closed on both sides (housing 200 is illustrated with an open side for clarity). Housing 200 may also have any other suitable regular or irregular shape. Central hub 210 is shown disposed near the substantial center of housing 200 and provides a surface for media strip 500 to wrap around. In addition, a bobbin or suitable alternative (not explicitly shown) wrapped with media strip 500 may be placed over central hub 210.

Separator 220 of housing 200 separates lower portion 202 of housing 200 from upper portion 204 of housing 200. Lower portion 202 may be sealed and remain sterile, thus keeping media strip 500 free from contamination. Upper portion 204 of housing 200 does not remain sterile during use since portions of media strip 500 that have contacted a patient or a medical device will pass therethrough. Thus, separator 220 will keep potential contaminants within upper portion 204 and prevent contaminants from entering lower portion 202 of housing 200, thus maintaining the sterility of lower portion 202.

A top piece 221 is included to cover upper portion 204 of housing 200. An aperture 222 (FIGS. 2 and 3) is disposed within top piece 221 and allows at least a portion of media strip 500 to exit housing 200, and more specifically, to exit upper portion 204 of housing 200.

Cover 230 is disposed near upper portion 204 of housing 200 and may be hingedly connected to housing 200. In such an embodiment, cover 230 is movable between a first position where cover 230 is in proximity with upper portion 204 of housing 200 (FIG. 2) and at least a second position where cover 230 is spaced apart from upper portion 204 of housing 200 (FIG. 1). Cover 230 covers aperture 222 in top piece 221, thus reducing the likelihood of outside contaminants entering housing 200.

Elongated tubular member 300 extends distally from housing 200 and includes a first lumen 310 and a second lumen 320 extending therethrough. At proximal portion 302 of elongated tubular member 300, lumens 310, 320 are illustrated as being separated a distance from each other, but it is envisioned that lumens 310, 320 may be closer together or farther apart than shown in the illustrated embodiment. First lumen 310 extends from lower portion 202 of housing 200 and second lumen 320 extends from upper portion 204 of housing 200. Distal portion 304 of elongated tubular member 300 is dimensioned and configured to be inserted into a patient through an incision, a trocar and/or an introducer (not explicitly shown). Further, in a disclosed embodiment, distal portion 304 of elongated tubular member 300 includes a rounded portion 305 (FIG. 4) adjacent first lumen 310 and/or adjacent second lumen 320, which facilitates the travel of media strip 500. It is envisioned that elongated tubular member 300 has a length in the range of about 10 inches to about 20 inches, and may be approximately equal to 15 inches. Other suitable lengths of elongated tubular member 300 are also contemplated. It is further envisioned that one lumen (e.g., first lumen 310) extends farther than another lumen (e.g., second lumen 320), as shown in FIG. 5. In such a configuration, distal portion 304 of elongated tubular member 300 would have a smaller diameter, thus enabling media-dispensing apparatus 100 to fit into a smaller incision.

It is envisioned that media-dispensing apparatus 100 includes a one-way passage valve 250 (FIG. 1). One-way passage valve 250 prohibits media strip 500 from traveling in a non-desired direction. One-way passage valve 250 may be disposed within housing 200, elongated tubular member 300 and/or an interface (not explicitly shown) therebetween. In the embodiment where one-way passage valve 250 is located within second lumen 320, one-way passage valve 250 precludes media strip 500 from traveling distally through second lumen 320 and/or proximally through first lumen 310. Thus, the non-sterile portion of media strip 500 that has already contacted a patient or medical device would be restricted from moving backwards into sterile first lumen 310 and/or into sterile lower portion 202 of housing 200. If first lumen 310 becomes contaminated, it would lose its sterility, thus reducing the utility of media-dispensing apparatus 100. One-way passage valve 250 may also be disposed within or incorporated into aperture 222.

Figure 4:
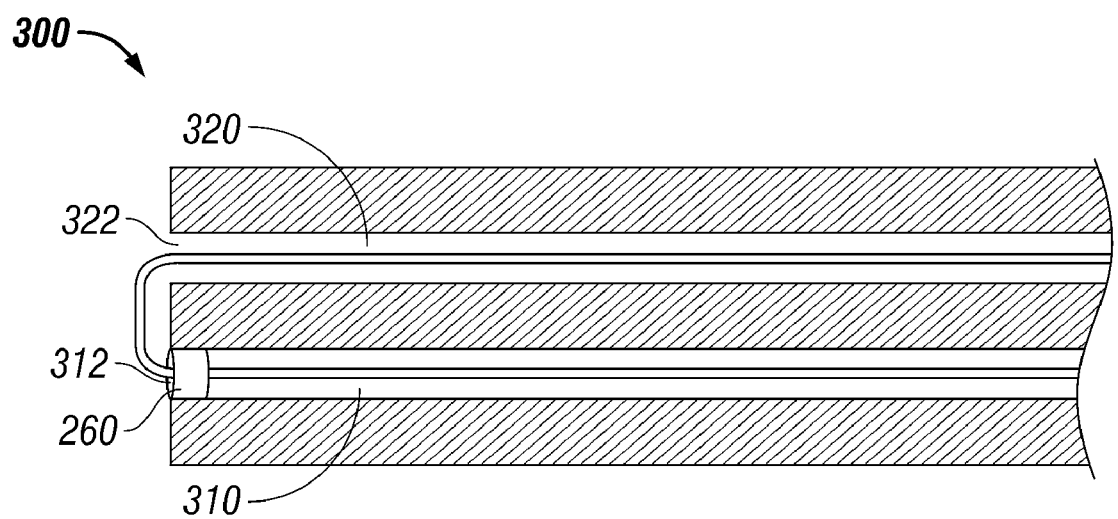
FIG. 4 is an enlarged cross-sectional view of a distal portion of an embodiment of an elongated tubular member of the media-dispensing apparatus of FIGS. 1-3, illustrated with a media strip therein.
Figure 5:
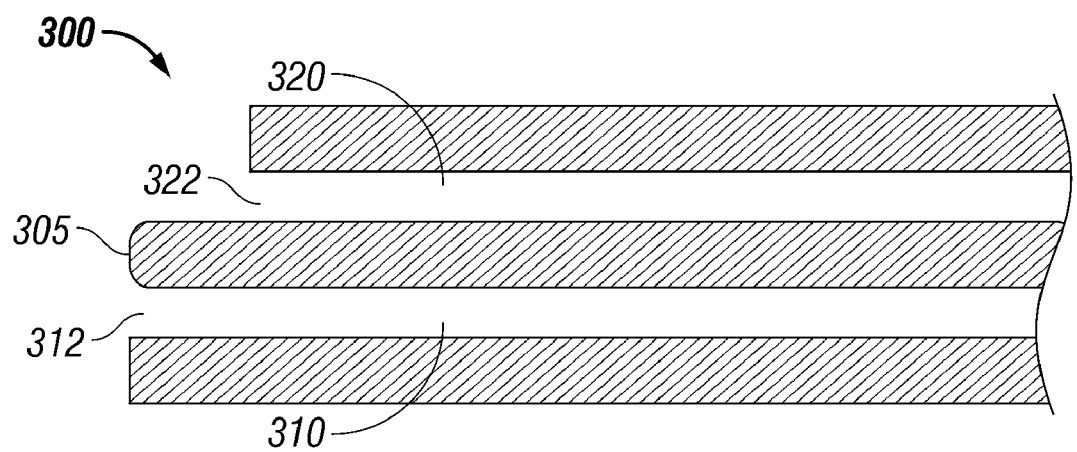
FIG. 5 is an enlarged cross-sectional view of a distal portion of an embodiment of an elongated tubular member of the media-dispensing apparatus of FIGS. 1-3, illustrated with one lumen extending farther distally than the other lumen.

With reference to FIG. 4, a seal 260 is illustrated disposed within first lumen 310 and adjacent a distal end 312 thereof. Within first lumen 310, seal 260 is operably configured to allow the distal passage of media strip 500, while preventing or limiting the proximal passage of other material (e.g., bacteria or body fluid from a surgical site). It is envisioned for seal 260 to be disposed in other suitable portions of media-dispensing apparatus 100.

A cutting instrument or knife 400 may be disposed near upper portion 204 of housing 200 (FIG. 1). Knife 400 facilitates cutting a portion of media strip 500. In the embodiment illustrated in FIG. 3, knife 400 is disposed within cover 230. In such an embodiment, it can be appreciated that the action of moving cover 230 from its second position towards its first position cuts a portion of media strip 500. It is further envisioned for knife 400 to be recessed within cover 230, thus reducing the likelihood that a person may be cut or that knife 400 may contact another instrument.

In operation, media strip 500 is disposed at least partially within media-dispensing apparatus 100. Media strip 500 wraps around central hub 210 (or on a bobbin inserted onto central hub), extends distally through first lumen 310, exits distal opening 306 of elongated tubular member 300, extends proximally through second lumen 320, and extends into upper portion 204 of housing 200 and through aperture 222 of top piece 221. To test a surgical site (e.g., body fluid, a medical device, etc.), a portion of elongated tubular member 300 of media-dispensing apparatus 100 is inserted into a patient near a surgical site via an introducer, trocar, etc. Media strip 500 is then pulled through aperture 222. Media strip 500 is pulled far enough away from aperture 222 so that at least a portion of media strip 500 that contacted the surgical site passes through aperture 222. Knife 400 may then be used to cut media strip 500. Indicia (not explicitly shown), may be disposed on media strip 500 and/or on media-dispensing apparatus 100 to aid a user in cutting media strip 500 at a proper location. Various testing methods may then be employed to test media strip 500. It is envisioned that media-dispensing apparatus 100 is left in contact with a surgical site for an extending period of time. Accordingly, a plurality of tests may be performed without removing media-dispensing apparatus 100 from the patient.

The method of the present disclosure includes providing media-dispensing apparatus 100 and performing the steps outlined above to test a patient and/or a surgical site for bacteria, contaminants, disease, etc. It is envisioned to use media-dispensing apparatus 100 to test for bacteria following an operative procedure, e.g., abdominal surgery.

It is envisioned that media strip 500 is comprised of litmus paper, another color-changing medium or any other suitable material to detect and/or identify abnormalities and/or infections. For example, the media strip 500 may be a protein polymer material that changes color after it contacts bacteria.

It is further envisioned that media strip 500 includes distance markers and/or perforations (not shown). Such distance markers and/or perforations may be appropriately spaced to notify the user how far media strip 500 must be pulled from aperture 222 to ensure that at least a portion of the media strip 500 that contacted the surgical site is removed from housing 200.

It is further envisioned that a fixed or removable cap (not shown) covers lower portion 202 and/or upper portion 204 of housing 200. Such a cap may fit over at least a majority of housing 200, thus reducing the likelihood of external contamination.

It will be understood that various modifications may be made to the embodiments disclosed herein. For example, a bore may be disposed through a portion of housing (e.g., through central hub). Therefore, the above description should not be construed as limiting, but merely as exemplifications of particular embodiments. Those skilled in the art will envision other modifications within the scope and spirit of the claims appended hereto.

The invention claimed is:

1. A method of testing body fluids, comprising the steps of:
providing a media-dispensing apparatus including a housing having a lower portion and an upper portion, an elongated tubular member extending distally from the housing and having a distal opening adjacent a distal end thereof, a first lumen disposed within the elongated tubular member extending from the lower portion of the housing to the distal opening, a second lumen disposed within the elongated tubular member extending from the upper portion of the housing to the distal opening, and a media strip extending from the lower portion of the housing, through the first lumen, out the distal opening of the elongated tubular member, through the second lumen and into the upper portion of the housing;
placing at least the distal opening of the elongated tubular member adjacent a surgical site such that a portion of the media strip contacts the surgical site; and
advancing the media strip such that the portion of the media strip that contacted the surgical site advances at least through the second lumen.

2. The method of testing body fluids according to claim 1, wherein the media-dispensing apparatus further includes a cover hingedly coupled to the housing and a cutting instrument disposed on a portion of at least one of the housing and the cover, the cover being moveable between a first position where the cover is in proximity with the upper portion of the housing and at least a second position where the cover is spaced apart from the upper portion of the housing, such that moving the cover from the second position towards the first position cuts the media strip and wherein the method further includes the step of cutting the media strip.

3. The method of testing body fluids according to claim 1, wherein at least the distal opening of the elongated tubular member remains adjacent the surgical site as the media strip is advanced.

4. The method of testing body fluids according to claim 1, wherein at least a portion of the media-dispensing apparatus is inserted near a patient's abdomen.

5. The method of testing body fluids according to claim 1, wherein the media-dispensing apparatus comprising a seal disposed within at least one of the first lumen and the second lumen, the seal being configured to allow the media strip to pass therethrough and being configured to limit the passage of body fluids during advancement of the media strip.

6. The method of claim 5, wherein the seal is disposed adjacent a distal end of the first lumen.

7. The method of testing body fluids according to claim 1, wherein one lumen of the media-dispensing apparatus extends farther distally than the other lumen.

8. The method of testing body fluids according to claim 1, wherein the media strip is made of a material which is able to at least detect or identify at least one abnormality or at least one infection.

9. The method of testing body fluids according to claim 1, wherein at least a portion of the media strip is a color changing medium.

* * * * *